(12) United States Patent
Langballe et al.

(10) Patent No.: US 6,174,856 B1
(45) Date of Patent: Jan. 16, 2001

(54) STABILIZED INSULIN COMPOSITIONS

(75) Inventors: Peter Langballe, Charlottenlund; Elsebeth Norup, Jyllinge, both of (DK)

(73) Assignee: Novo Nordisk A/S, Bagsvaerd (DK)

( * ) Notice: Under 35 U.S.C. 154(b), the term of this patent shall be extended for 0 days.

(21) Appl. No.: 09/227,053

(22) Filed: Jan. 7, 1999

Related U.S. Application Data

(60) Provisional application No. 60/071,336, filed on Jan. 14, 1998, now abandoned.

(30) Foreign Application Priority Data

Jan. 9, 1998 (EP) .................................................. 98610001

(51) Int. Cl.$^7$ .............................. A61K 38/28; C07K 14/62
(52) U.S. Cl. .............................. 514/4; 530/303; 530/304; 530/305; 514/3; 514/12
(58) Field of Search ..................... 514/3, 4, 12; 530/303, 530/304, 305

(56) References Cited

U.S. PATENT DOCUMENTS

| | | | |
|---|---|---|---|
| 4,472,385 | * 9/1984 | Brange et al. | ........................ 424/178 |
| 5,070,186 | * 12/1991 | Joergensen | ........................... 530/304 |
| 5,177,058 | * 1/1993 | Dorschug | .................................. 514/4 |
| 5,474,978 | * 12/1995 | Bakaysa et al. | ......................... 514/3 |
| 5,750,497 | * 5/1998 | Hanelund et al. | ....................... 514/3 |

FOREIGN PATENT DOCUMENTS

| | | |
|---|---|---|
| 0 060 141 | 9/1982 | (EP) . |
| 0 681 833 | 11/1995 | (EP) . |
| WO 95/00550 | 1/1995 | (WO) . |
| WO 97/48414 | 12/1997 | (WO) . |

OTHER PUBLICATIONS

Uchida Ichio, Patent Abstract of Japan, No. 01287463 (Nov. 29, 1989).
Storm et al., Biochemistry, vol. 24, pp. 1749–1756 (1985).

* cited by examiner

Primary Examiner—F. T. Moezie
(74) Attorney, Agent, or Firm—Steve T. Zelson, Esq.; Elia J. Lambiris, Esq.

(57) ABSTRACT

An aqueous insulin composition with improved chemical and physical stability comprising human insulin or an analogue or derivative thereof, a buffer selected from glycylglycine, citrate or TRIS, in particular glycylglycine, and metal ions, in particular calcium or magnesium ions.

19 Claims, 2 Drawing Sheets

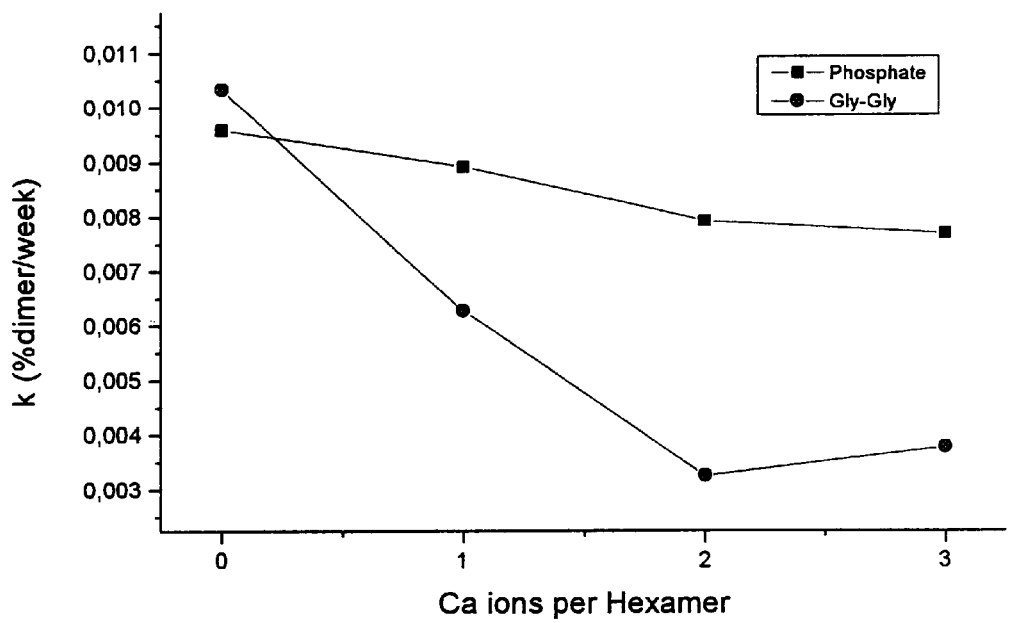
Figure 1. k (%dimer/week) as a function of $Ca^{2+}/(NN304)_6(Zn^{2+})_2$ at 4 °C.
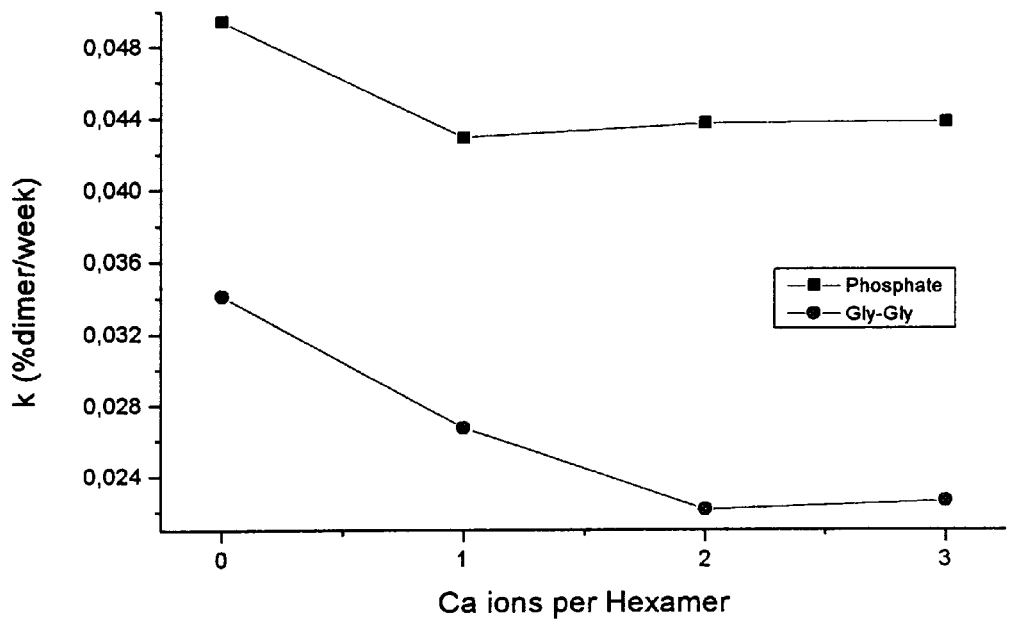
Figure 2. k (%dimer/week) as a function of $Ca^{2+}/(NN304)_6(Zn^{2+})_2$ at 25 °C.

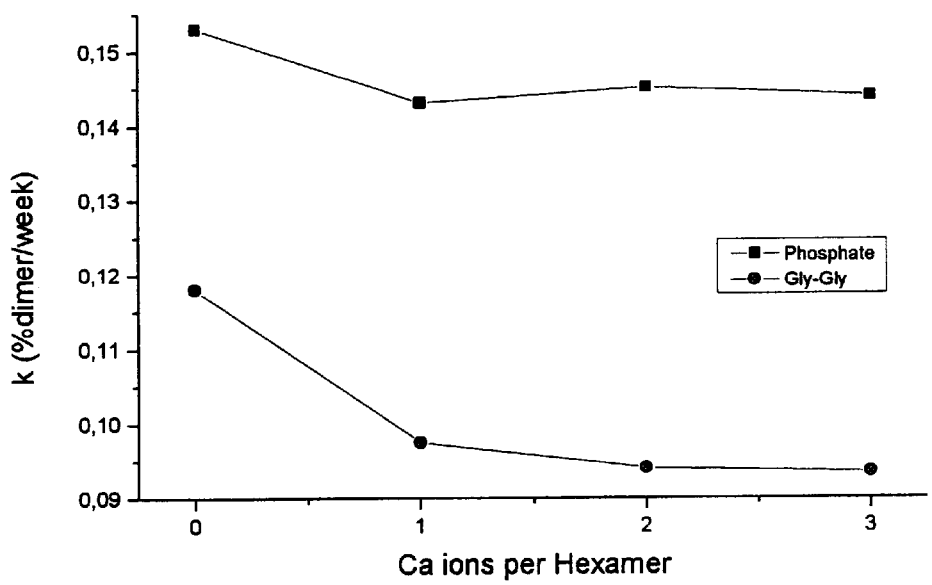
Figure 3. k (%dimer/week) as a function of $Ca^{2+}/(NN304)_6(Zn^{2+})_2$ at 37 °C.
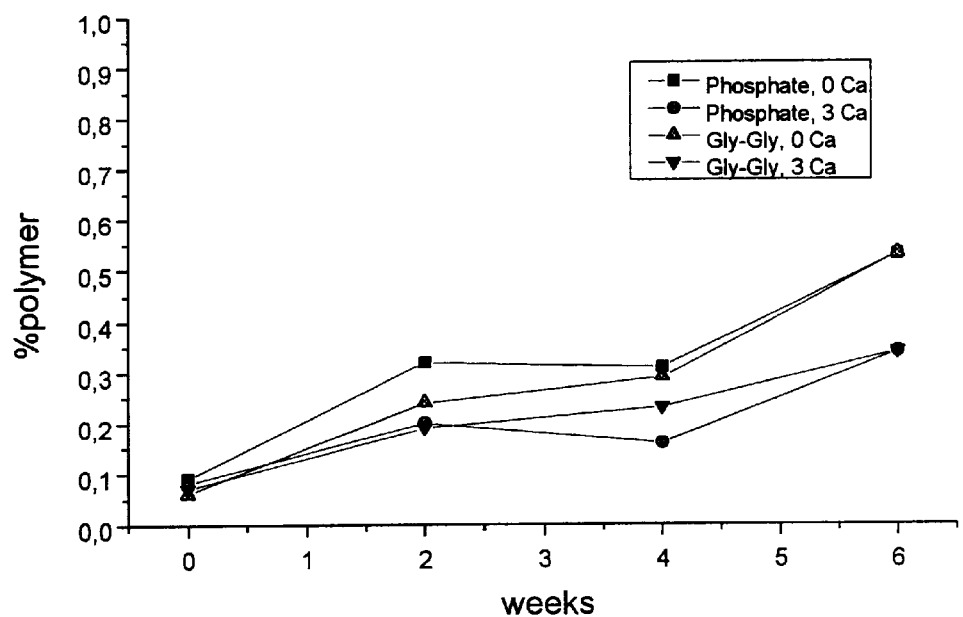
Figure 4. %polymer as function of time for the two buffer systems with 0 and 3 $Ca^{2+}/(NN304)_6(Zn^{2+})_2$ at 37 °C.

STABILIZED INSULIN COMPOSITIONS

CROSS-REFERENCE TO RELATED APPLICATIONS

This application claims priority under 35 U.S.C. 119 of U.S. provisional application 60/071,336 filed Jan. 14, 1998 now abandoned and European application EP 98610001.4 filed Jan. 9, 1998, the contents of which are fully incorporated herein by reference.

FIELD OF THE INVENTION

The present invention relates to stabilized pharmaceutical compositions comprising insulin or an analogue or derivative thereof. The invention also relates to parenteral formulations comprising such insulin compositions and to a method for improving the stability of insulin compositions.

BACKGROUND OF THE INVENTION

Diabetes mellitus is a metabolic disorder in which the ability to utilize glucose is more or less completely lost. About 2% of all people suffer from diabetes.

Since the discovery of insulin in the 1920's, continuous strides have been made to improve the treatment of diabetes mellitus. To help avoid extreme glucose levels, diabetic patients often practice insulin replacement therapy, whereby insulin is administered by injection.

In the treatment of diabetes mellitus, many varieties of insulin compositions have been suggested and used, including regular insulin, Semilente® insulin, isophane insulin, insulin zinc suspensions, protamine zinc insulin, and Ultralente® insulin. As diabetic patients typically are treated with insulin for several decades, there is a major need for safe and life quality improving insulin compositions. Some of the commercially available insulin compositions are characterized by a fast onset of action, while other compositions have a relatively slow onset but show a more or less prolonged action. Fast acting insulin compositions are usually solutions of insulin, while retarded acting insulin compositions can be suspensions containing insulin in crystalline and/or amorphous form precipitated by addition of zinc salts alone or by addition of protamine or by a combination of both. In addition, some patients use compositions having both a fast onset of action and a more prolonged action. Such a composition may be an insulin solution wherein protamine insulin crystals are suspended. Some patients prepare the final composition themselves by mixing an insulin solution with a suspension composition in the desired ratio.

Human insulin consists of two polypeptide chains, the so-called A and B chains, which contain 21 and 30 amino acid residues, respectively. The A and B chains are interconnected by two cystine disulphide bridges. Insulin from most other species has a similar construction, but may not contain the same amino acid residues at corresponding positions.

The development of genetic engineering has made it possible to easily prepare a great variety of insulin compounds analogous to human insulin. In these insulin analogues, one or more of the amino acid residues have been substituted with other amino acid residues which can be coded for by the nucleotide sequences. Since human insulin, as explained above, contains 51 amino acid residues, it is obvious that a large number of insulin analogues is possible, and a great variety of analogues with interesting properties have been prepared. In human insulin solutions with a concentration of interest for injectable compositions, the insulin molecule is present in associated form as a hexamer (Brange et al. Diabetes Care 13, (1990), 923–954). After subcutaneous injection, it is believed that the rate of absorption by the blood stream is dependent on the size of the molecule, and it has been found that insulin analogues with amino acid residue substitutions which counteract or inhibit this hexamer formation have an unusually fast onset of action (Brange et al.: Ibid). This can be of great therapeutic value for the diabetic patient.

A general survey of pharmaceutical compositions containing insulin is given by Brange et al. in Galenics of Insulin, Springer-Verlag (Berlin, 1987).

Pharmaceutical compositions which are based on analogues of human insulin have e.g. been presented by Heinemann et al., Lutterman et al. and Wiefels et al. at the "Frontiers in Insulin Pharmacology" International Symposium in Hamburg, 1992.

U.S. Pat. No. 5,474,978 discloses a rapidly acting parenteral formulation comprising a human insulin analogue hexamer complex consisting of six monomeric insulin analogues, zinc ions and at least three molecules of a phenolic derivative.

Normally, insulin compositions are administered by subcutaneous injection. What is important for the patient is the profile of action of the insulin composition, i.e. the action of insulin on the glucose metabolism as a function of the time from the injection, including the time for the onset of insulin action, the maximum value and the total duration of action. A variety of insulin compositions with different profiles of action are required by patients. An individual patient may thus on the same day use insulin compositions with very different profiles of action. The profile of action required for any given patient at any given time depends upon several factors, e.g. the time of the day and the amount and composition of any meal eaten by the patient.

Also important for the patient is the chemical stability of the insulin compositions, especially due to the abundant use of pen-like injection devices such as devices which contain Penfill® cartridges, in which an insulin composition is stored until the entire cartridge is empty. This may last 1 to 2 weeks or more for devices containing a 1.5 or 3.0 ml cartridge. During storage, covalent chemical changes in the insulin structure occur. This may lead to the formation of molecules which are less active and potentially immunogenic such as deamidation products and higher molecular weight transformation products (dimers, polymers, etc.). A comprehensive study on the chemical stability of insulin is given in by Jens Brange in "Stability of Insulin", Kluwer Academic Publishers, 1994.

Compositions comprising insulin and insulin analogues are traditionally formulated using various additives, for example sodium phosphate (buffer), $Zn^{2+}$ (stabilizer), phenol/m-cresol (preservative and stabilizer), sodium chloride (tonicity agent and stabilizer), and glycerol/mannitol (tonicity agents).

The shelf-life of insulin products is mainly compromised by the formation of soluble aggregates (dimers and polymers) over time, despite the fact that insulin is typically stored at a low temperature of no more than about 5° C., which improves the shelf-life considerably compared to storage e.g. at room temperature. In addition, insulin products are subject to the formation of insoluble aggregates (fibrils) as a result of shaking, e.g. when carried in the pocket of a patient or during transport. It is essential for the quality of an insulin product that the tendency to form such soluble and insoluble aggregates as a result of chemical or physical influences is reduced to an absolute minimum.

Although progress has been made in the chemical and physical stabilization of insulin-containing compositions, the need still remains for improving the shelf-life of such products as well as their in-use time at temperatures of about 20–37° C., i.e. from room temperature to body temperature.

Acta Pharmaceutica Nordica 4(4), 1992, pp. 149–158 discloses insulin compositions with a sodium chloride concentration in the range of 0 to 250 mM. The major part of the compositions, including those which additionally comprise glycerol, contain a rather high amount of sodium chloride, i.e. 0.7%, corresponding approximately to a concentration of 120 mM.

PCT/DK97/00268 (Novo Nordisk A/S) discloses insulin compositions having improved chemical stability, the compositions comprising a combination of glycerol and/or mannitol and 5–100 mM of a halogenide, e.g. sodium chloride.

Storm & Dunn ("The Glu(B13) carboxylates of the insulin hexamer form a cage for $Cd^{2+}$ and $Ca^{2+}$ ions", *Biochemistry* 1985, 24, 1749–1756) performed studies showing that the highly co-operative zinc-insulin hexamer $(In)_6(Zn^{2+})_2$ is further modulated by calcium binding, because the six Glu-(B13) residues within the hexamer structure form a cage that binds calcium and cadmium ions. The single binding site is stated to bind $Ca^{2+}$ and $Cd^{2+}$ with high affinity and to be specific for these two ions.

SUMMARY OF THE INVENTION

It has now surprisingly been found that the stability of insulin compositions can be significantly improved by formulating the compositions using a combination of a buffer such as glycylglycine (Gly—Gly) and metal ions such as $Ca^{2+}$. It has in particular been found that when the sodium phosphate buffer in a traditional insulin composition is replaced with a Gly—Gly buffer in combination with calcium ions, the formation of soluble aggregates during storage at 5° C. decreased remarkably. This is especially surprising in view of the fact that a separate replacement of sodium phosphate by Gly—Gly was not found to have any effect, and that a separate addition of calcium to a composition containing a sodium phosphate buffer only had a minor effect. It was further found that compositions containing the combination of Gly—Gly and calcium also showed a reduced tendency to form insoluble aggregates during shaking.

It is an object of the present invention to provide pharmaceutical compositions comprising insulin or an analogue or derivative thereof which have improved chemical and physical stability compared to known insulin compositions.

In one aspect, the invention therefore relates to an aqueous insulin composition comprising human insulin or an analogue or derivative thereof, at least one buffer selected from the group consisting of glycylglycine, citrate and TRIS, and metal ions selected from the group consisting of calcium and magnesium, with the proviso that when the buffer is TRIS, the concentration of metal ions is not in the range of 0.0004–0.01 M.

Another aspect of the invention relates to a parenteral pharmaceutical formulation comprising an insulin composition of the invention as defined above.

A further aspect of the invention relates to a method for improving the stability of an insulin composition comprising human insulin or an analogue or a derivative thereof, the method comprising adding to said composition at least one buffer selected from the group consisting of glycylglycine, citrate and TRIS, and metal ions selected from the group consisting of calcium and magnesium, with the proviso that when the buffer is TRIS, the concentration of metal ions is not in the range of 0.0004–0.01 M.

BRIEF DESCRIPTION OF THE DRAWINGS

FIG. 1 is a graph showing k (% dimer/week) as a function of $Ca^{2+}/(NN304)_6(Zn^{2+})_2$ at 4° C.;

FIG. 2 is a graph showing k (% dimer/week) as a function of $Ca^{2+}/(NN304)_6(Zn^{2+})_2$ at 25° C.;

FIG. 3 is a graph showing k (% dimer/week) as a function of $Ca^{2+}/(NN304)_6(Zn^{2+})_2$ at 37° C.; and FIG. 4 is a graph showing the % polymer as a function of time for the phosphate and Gly—Gly buffer systems with 0 and 3 $Ca^{2+}/(NN304)_6(Zn^{2+})_2$ at 37° C.

DETAILED DESCRIPTION OF THE INVENTION

Unless otherwise specified, the term "insulin" as used herein is intended to refer to not only human insulin as such, but also insulin analogues and derivatives thereof.

The term "analogue of human insulin" as used herein refers to a polypeptide having the amino acid residue sequence of human insulin in which one or more amino acid residues have been deleted and/or replaced by other amino acid residues, including amino acid residues not encoded by the genetic code, or comprising additional amino acid residues, i.e. more than the 51 amino acid residues of human insulin.

The term "derivative of human insulin" as used herein refers to human insulin or an analogue thereof in which at least one organic substituent is bound to one or more of the amino acid residues.

The term "aqueous" as used herein refers to the fact that the insulin compositions of the present invention will be water-based, but it will be clear that the compositions may optionally contain additional solvents, e.g. a small amount of a water-miscible solvent.

The term "chemical stability" as used herein refers to the tendency of an insulin composition to form soluble aggregates of insulin during storage under static conditions, including storage at low temperatures of approximately 4–5° C. The term "physical stability" as used herein refers to the tendency of an insulin composition to form insoluble aggregates of insulin as a result of a physical action such as shaking of an insulin composition.

In the present context, the unit "U" corresponds to 6 nmol of insulin.

Insulin compositions according to the invention have been shown to have a high chemical and physical stability, which is reflected in a reduction in the formation of soluble and insoluble aggregates after storage and/or shaking.

The present invention is particularly advantageous in connection with compositions comprising analogues and/or derivatives of human insulin. Thus, the insulin composition according to the invention preferably comprises one or more fast-acting analogues of human insulin, in particular analogues wherein the amino acid residue at position B28 is Asp, Lys, Leu, Val or Ala and the amino acid residue at position B29 is Lys or Pro; or des(B28–B30), des(B27) or des(B30) human insulin. The insulin analogue is preferably selected from analogues of human insulin wherein the amino acid residue at position B28 is Asp or Lys, and the amino acid residue at position B29 is Lys or Pro. The most preferred analogues are $Asp^{B28}$ human insulin and $Ly^{B28}Pro^{B29}$ human insulin.

In another embodiment the insulin composition according to the invention comprises an insulin derivative having a protracted profile of action, such an insulin having one or more lipophilic substituents. The preferred lipophilic insulins are acylated insulins, including those described in WO 95/07931 (Novo Nordisk A/S), e.g. human insulin derivatives wherein the ε-amino group of $Lys^{B29}$ contains an acyl substituent which comprises at least 6 carbon atoms.

The following are preferred insulin derivatives: $N^{\epsilon B29}$-myristoyl-des(B30) human insulin, $N^{\epsilon B29}$-palmitoyl-des(B30) human insulin, $N^{\epsilon B29}$-myristoyl human insulin, $N^{\epsilon B29}$-palmitoyl human insulin, $N^{\epsilon B28}$-myristoyl $Lys^{B28}$ $Pro^{B29}$ human insulin, $N^{\epsilon B28}$-palmitoyl $Lys^{B28}$ $Pro^{B29}$ human insulin, $N^{\epsilon B30}$-myristoyl-$Thr^{B29}Lys^{B30}$ human insulin, $N^{\epsilon B30}$-palmitoyl-$Thr^{B29}Lys^{B30}$ human insulin, $N^{\epsilon B29}$-(N-palmitoyl-γ-glutamyl)-des (B30) human insulin, $N^{\epsilon B29}$-(N-lithocholyl-γ-glutamyl)-des(B30) human insulin, $N^{\epsilon B29}$-(ω-carboxyheptadecanoyl)-des(B30) human insulin, and $N^{\epsilon B29}$-(ω-carboxyheptadecanoyl) human insulin; the most preferred being $N^{\epsilon B29}$-myristoyl-des(B30) human insulin.

Insulin compositions according to the invention will normally contain about 60 to 3000 nmol/ml, preferably 240 to 1200 nmol/ml, of human insulin or insulin analogue or derivative.

The amount of metal ions to be incorporated into compositions according to the invention is typically in the range of about 0.1–10, more preferably about 0.5–5, e.g. about 1–4 metal ions per hexamer of insulin or insulin analogue or derivative. Particularly good results have been obtained with about 2–3 metal ions per hexamer.

The metal ions should be pharmaceutically acceptable and are in particular calcium and/or magnesium. A preferred metal ion is calcium, as this has been shown to provide surprising and advantageous results in terms of stabilisation of insulin compositions containing Gly—Gly. However, it is also contemplated that other pharmaceutically acceptable metal ions having properties (size, valence) similar to calcium will also be suitable, in particular magnesium.

The concentration of the buffer, preferably Gly—Gly, will typically be in the range of about 1–20 mM, preferably about 3–15 mM, such as about 4–10 mM, e.g. about 5–7 mM.

In another embodiment, the insulin composition may comprise 5 to 100 mM, more preferably 10 to 100 mM, e.g. 10 to 70 mM, of a halide, as described in PCT/DK97/00268.

In a particular embodiment, the insulin composition of the invention comprises insulin or an insulin analogue as well as an insulin derivative.

In a particular embodiment of the invention, the insulin composition comprises, in addition to metal ions and a buffer such as Gly—Gly as described above: 60 to 3000 nmol/ml, preferably 240 to 1200 nmol/ml, of human insulin or insulin analogue or derivative, 10 to 40 μg Zn/100 U insulin, preferably 10 to 26 μg Zn/100 U insulin, and 0 to 5 mg/ml, preferably 0 to 4 mg/ml, of a phenolic compound.

As a phenolic compound, 0.5 to 4.0 mg/ml, preferably 0.6 to 4.0 mg/ml, of m-cresol or 0.5 to 4.0 mg/ml, preferably 1.4 to 4.0 mg/ml, of phenol, or a mixture thereof, is advantageously employed.

The insulin composition of the present invention may furthermore contain other ingredients common to insulin compositions, for example zinc complexing agents such as citrate, or an additional buffer such as a phosphate buffer. When citrate is present, it may thus be present to function as a buffer and/or a zinc complexing agent.

The present invention furthermore relates to a parenteral pharmaceutical formulation comprising an insulin composition of the invention.

Moreover, the present invention is concerned with a method for improving the stability of an insulin composition comprising human insulin or an analogue or a derivative thereof, which method comprises adding at least one buffer selected from the group consisting of glycylglycine, citrate and TRIS and metal ions selected from the group consisting of calcium and magnesium to said composition, with the proviso that when the buffer is TRIS, the concentration of metal ions is not in the range of 0.0004–0.01 M.

The invention is further illustrated by the following non-limiting examples.

EXAMPLE 1

Materials and Methods

The composition of the test systems is given below; the buffer and calcium ion concentrations used are given in Table 1 below.

| | |
|---|---|
| Insulin ("NN304")* | 0.6 μmol |
| Phenol | 1.50 mg |
| m-Cresol | 1.72 mg |
| Mannitol | 35 mg |
| Sodium chloride | 1.17 mg |
| Zinc acetate | 13.1 μg $Zn^{2+}$ (2 $Zn^{2+}$ per $(NN304)_6$) |
| Calcium chloride, dihydrate | see Table 1 |
| Buffer substance | see Table 1 |
| NaOH | for pH adjustment |
| HCl | for pH adjustment |
| Water to make | 1 ml |
| pH = 7.5 | |

*NN304 is insulin analogue $N^{\epsilon B29}$-myristoyl-des(B30) human insulin.

TABLE 1

Concentration of buffer substance and $Ca^{2+}$ for the test systems

| Test system | di-Sodium hydrogen phosphate, dihydrate (mM) | Glycylglycin (mM) | $Ca^{2+}$ $(Ca^{2+}/(NN304)_6)$ |
|---|---|---|---|
| Phosphate, 0 $Ca^{2+}$ | 7 | 0 | 0 |
| Phosphate, 1 $Ca^{2+}$ | 7 | 0 | 1 |
| Phosphate, 2 $Ca^{2+}$ | 7 | 0 | 2 |
| Phosphate, 3 $Ca^{2+}$ | 7 | 0 | 3 |
| Gly-Gly, 0 $Ca^{2+}$ | 0 | 7 | 0 |
| Gly-Gly, 1 $Ca^{2+}$ | 0 | 7 | 1 |
| Gly-Gly, 2 $Ca^{2+}$ | 0 | 7 | 2 |
| Gly-Gly, 3 $Ca^{2+}$ | 0 | 7 | 3 |

Experimental Procedure 50 ml of each test system were prepared. Insulin analogue NN304 was dissolved in water (2–10° C.). Immediately after dissolution of NN304 solutions containing $Zn^{2+}$, $Ca^{2+}$, phenol+m-cresol+mannitol and buffer substance+NaCl were added. The pH value was adjusted by addition of HCl/NaOH, and water was added to make the final volume. The test systems were dispensed in 1.5 ml cartridges after sterile filtration (Sterivex GV 0.22μ). The cartridges were placed at 4° C., 25° C. or 37° C. Samples were taken and analyzed for formation of dimers and polymers as well as for other impurities in the form of related proteins examined by liquid chromatography (referred to below as "RP impurities", i.e.

impurities detectable by reverse phase HPLC). pH was also measured to determine the buffer effect. The analytical methods used in this study were Size Exclusion Chromatography and Reverse Phase Chromatography.

Results and Discussion

Dimer Formation

The values obtained for % dimer and the calculated values of k (% dimer/week) at 4, 25 and 37° C. are listed in Table 2, 3 and 4, respectively. k is calculated by means of a linear regression. The listed values of R (correlation coefficient) indicate a rather good linear correlation between % dimer and storage time for the observation periods used. k is presented in the attached FIGS. 1, 2 and 3 as a function of the $Ca^{2+}$ concentration.

The tables and figures show that the $Ca^{2+}$ concentration has a greater effect on k (% dimer/week) for the Gly—Gly system compared to the phosphate system. The effect of $Ca^{2+}$ is most pronounced at 4° C. An addition of 2–3 $Ca^{2+}$ per $(NN304)_6(Zn^{2+})_2$ thus causes a decrease of k to about one-third of the value without $Ca^{2+}$ at 4° C. for the Gly—Gly system, but only about a 20% decrease for the phosphate system. The rate of dimer formation is approximately identical for the two buffer systems without $Ca^{2+}$. The more pronounced effect of $Ca^{2+}$ for the Gly—Gly system is believed to be due to a stronger binding between $Ca^{2+}$ and phosphate than between $Ca^{2+}$ and Gly—Gly. It is interesting to note that replacing phosphate with Gly—Gly causes a significant decrease of k at 25 and 37° C. for a system without $Ca^{2+}$, but not at 4° C., which is the preferred storage temperature among the three temperatures tested.

TABLE 2

Formation of dimer at 4° C.

| Test system | Storage time (weeks) | | | | | k (% dimer/week) | R |
|---|---|---|---|---|---|---|---|
| | 0 (% dimer) | 10 (% dimer) | 14 (% dimer) | 18 (% dimer) | 28 (% dimer) | | |
| Phosphate 0 $Ca^{2+}$ | 0.19 | 0.29 | 0.30 | 0.36 | 0.46 | 0.00958 | 0.993 |
| Phosphate 1 $Ca^{2+}$ | 0.17 | 0.26 | 0.27 | 0.33 | 0.42 | 0.00892 | 0.993 |
| Phosphate 2 $Ca^{2+}$ | 0.18 | 0.26 | 0.26 | 0.33 | 0.40 | 0.00792 | 0.984 |
| Phosphate 3 $Ca^{2+}$ | 0.17 | 0.23 | 0.26 | 0.31 | 0.38 | 0.00769 | 0.993 |
| Gly—Gly 0 $Ca^{2+}$ | 0.17 | 0.30 | 0.30 | 0.38 | 0.46 | 0.0103 | 0.987 |
| Gly—Gly 1 $Ca^{2+}$ | 0.19 | 0.23 | 0.26 | 0.30 | 0.36 | 0.00627 | 0.988 |
| Gly—Gly 2 $Ca^{2+}$ | 0.18 | 0.21 | 0.21 | 0.24 | 0.27 | 0.00325 | 0.980 |
| Gly—Gly 3 $Ca^{2+}$ | 0.17 | 0.19 | 0.20 | 0.24 | 0.27 | 0.00377 | 0.962 |

TABLE 3

Formation of dimer at 25° C.

| Test system | Storage time (weeks) | | | | k (% dimer/week) | R |
|---|---|---|---|---|---|---|
| | 0 (% dimer) | 4 (% dimer) | 6 (% dimer) | 8 (% dimer) | | |
| Phosphate 0 $Ca^{2+}$ | 0.19 | 0.36 | 0.49 | 0.58 | 0.0494 | 0.997 |
| Phosphate 1 $Ca^{2+}$ | 0.17 | 0.34 | 0.41 | 0.52 | 0.0429 | 0.998 |
| Phosphate 2 $Ca^{2+}$ | 0.18 | 0.34 | 0.46 | 0.52 | 0.0437 | 0.995 |
| Phosphate 3 $Ca^{2+}$ | 0.17 | 0.34 | 0.46 | 0.50 | 0.0430 | 0.991 |
| Gly—Gly 0 $Ca^{2+}$ | 0.17 | 0.26 | 0.39 | 0.43 | 0.0341 | 0.976 |
| Gly—Gly 1 $Ca^{2+}$ | 0.19 | 0.24 | 0.34 | 0.40 | 0.0267 | 0.960 |
| Gly—Gly 2 $Ca^{2+}$ | 0.18 | 0.22 | 0.29 | 0.36 | 0.0221 | 0.954 |
| Gly—Gly 3 $Ca^{2+}$ | 0.17 | 0.21 | 0.29 | 0.35 | 0.0226 | 0.956 |

TABLE 4

Formation of dimer at 37° C.

| Test system | Storage time (weeks) | | | | k (% dimer/week) | R |
|---|---|---|---|---|---|---|
| | 0 (% dimer) | 4 (% dimer) | 6 (% dimer) | 8 (% dimer) | | |
| Phosphate 0 $Ca^{2+}$ | 0.19 | 0.54 | 0.81 | 1.12 | 0.153 | 0.999 |
| Phosphate 1 $Ca^{2+}$ | 0.17 | 0.53 | 0.72 | 1.06 | 0.143 | 0.994 |
| Phosphate 2 $Ca^{2+}$ | 0.18 | 0.49 | 0.74 | 1.06 | 0.145 | 0.999 |
| Phosphate 3 $Ca^{2+}$ | 0.17 | 0.50 | 0.74 | 1.05 | 0.144 | 0.998 |
| Gly—Gly 0 $Ca^{2+}$ | 0.17 | 0.33 | 0.56 | 0.88 | 0.118 | 0.989 |
| Gly—Gly 1 $Ca^{2+}$ | 0.19 | 0.33 | 0.48 | 0.79 | 0.0975 | 0.979 |
| Gly—Gly 2 $Ca^{2+}$ | 0.18 | 0.32 | 0.46 | 0.76 | 0.0940 | 0.979 |
| Gly—Gly 3 $Ca^{2+}$ | 0.17 | 0.30 | 0.43 | 0.75 | 0.0935 | 0.970 |

Polymer

The values obtained for % polymer at 4, 25 and 37° C. are listed in Tables 5, 6 and 7. % polymer as a function of time is presented in the attached FIG. 4 at 37° C. for the two buffer systems with 0 and 3 $Ca^{2+}/(NN304)_6(Zn^{2+})_2$. Tables 5 and 6 show that polymer formation is negligible at 4 and 25° C. for the tested observation periods. The polymer formation is considerable at 37° C. and is decreased by about 30% by addition of 2–3 $Ca^{2+}/(NN304)_6(Zn^{2+})_2$ for both systems after 6 weeks of storage (Table 7 and FIG. 4).

TABLE 5

Formation of polymer at 4° C.

| Test system | Storage time (weeks) | | | | |
|---|---|---|---|---|---|
| | 0 (% polymer) | 10 (% polymer) | 14 (% polymer) | 18 (% polymer) | 28 (% polymer) |
| Phosphate 0 $Ca^{2+}$ | 0.09 | 0.06 | 0.07 | 0.07 | 0.09 |
| Phosphate 1 $Ca^{2+}$ | 0.07 | 0.06 | 0.08 | 0.06 | 0.09 |
| Phosphate 2 $Ca^{2+}$ | 0.07 | 0.06 | 0.08 | 0.06 | 0.07 |
| Phosphate 3 $Ca^{2+}$ | 0.08 | 0.07 | 0.07 | 0.06 | 0.08 |
| Gly—Gly 0 $Ca^{2+}$ | 0.06 | 0.05 | 0.07 | 0.08 | 0.12 |
| Gly—Gly 1 $Ca^{2+}$ | 0.10 | 0.05 | 0.06 | 0.06 | 0.09 |
| Gly—Gly 2 $Ca^{2+}$ | 0.08 | 0.06 | 0.07 | 0.06 | 0.08 |
| Gly—Gly 3 $Ca^{2+}$ | 0.07 | 0.05 | 0.06 | 0.06 | 0.08 |

TABLE 6

Formation of polymer at 25° C.

| Test system | Storage time (weeks) | | | |
|---|---|---|---|---|
| | 0 (% polymer) | 4 (% polymer) | 6 (% polymer) | 8 (% polymer) |
| Phosphate 0 $Ca^{2+}$ | 0.09 | 0.09 | 0.15 | 0.09 |
| Phosphate 1 $Ca^{2+}$ | 0.07 | 0.09 | 0.11 | 0.10 |
| Phosphate 2 $Ca^{2+}$ | 0.07 | 0.09 | 0.11 | 0.09 |
| Phosphate 3 $Ca^{2+}$ | 0.08 | 0.08 | 0.13 | 0.10 |
| Gly-Gly 0 $Ca^{2+}$ | 0.06 | 0.10 | 0.11 | 0.13 |
| Gly-Gly 1 $Ca^{2+}$ | 0.10 | 0.10 | 0.14 | 0.11 |
| Gly-Gly 2 $Ca^{2+}$ | 0.08 | 0.10 | 0.11 | 0.10 |
| Gly-Gly 3 $Ca^{2+}$ | 0.07 | 0.11 | 0.16 | 0.09 |

TABLE 7

Formation of polymer at 37° C.

| Test system | Storage time (weeks) | | | |
|---|---|---|---|---|
| | 0 (% polymer) | 2 (% polymer) | 4 (% polymer) | 6 (% polymer) |
| Phosphate 0 $Ca^{2+}$ | 0.09 | 0.32 | 0.30 | 0.53 |
| Phosphate 1 $Ca^{2+}$ | 0.07 | 0.24 | 0.26 | 0.39 |
| Phosphate 2 $Ca^{2+}$ | 0.07 | 0.25 | 0.16 | 0.35 |
| Phosphate 3 $Ca^{2+}$ | 0.08 | 0.20 | 0.16 | 0.34 |
| Gly-Gly 0 $Ca^{2+}$ | 0.06 | 0.24 | 0.29 | 0.53 |
| Gly-Gly 1 $Ca^{2+}$ | 0.10 | 0.24 | 0.27 | 0.42 |
| Gly-Gly 2 $Ca^{2+}$ | 0.08 | 0.17 | 0.21 | 0.38 |
| Gly-Gly 3 $Ca^{2+}$ | 0.07 | 0.19 | 0.23 | 0.34 |

RP-Purity

The values obtained for % impurities detectable by reverse phase HPLC at 4, 25 and 37° C. are listed in Tables 8, 9 and 10. $Ca^{2+}$ has no or perhaps only a small effect on the formation of RP-impurities. Table 10 shows a slightly increased amount of RP-impurities for the Gly—Gly systems compared to the phosphate systems after 6 weeks of storage at 37° C., but there are no apparent differences at 4 or 25° C.

TABLE 8

Formation of RP-impurities at 4° C.

| Test system | Storage time (weeks) | |
|---|---|---|
| | 0 (% impurities) | 10 (% impurities) |
| Phosphate 0 $Ca^{2+}$ | 2.4 | 2.3 |
| Phosphate 1 $Ca^{2+}$ | 2.3 | 2.3 |
| Phosphate 2 $Ca^{2+}$ | 2.4 | 2.3 |
| Phosphate 3 $Ca^{2+}$ | 2.2 | 2.0 |
| Gly-Gly 0 $Ca^{2+}$ | 2.3 | 2.3 |
| Gly-Gly 1 $Ca^{2+}$ | 2.1 | 2.3 |
| Gly-Gly 2 $Ca^{2+}$ | 2.3 | 2.1 |
| Gly-Gly 3 $Ca^{2+}$ | 2.0 | 2.2 |

TABLE 9

Formation of RP-impurities at 25° C.

| Test system | Storage time (weeks) | | | |
|---|---|---|---|---|
| | 0 (% impurities) | 4 (% impurities) | 6 (% impurities) | 8 (% impurities) |
| Phosphate 0 $Ca^{2+}$ | 2.4 | 2.3 | 2.8 | 2.8 |
| Phosphate 1 $Ca^{2+}$ | 2.3 | 2.4 | 2.5 | 2.9 |
| Phosphate 2 $Ca^{2+}$ | 2.4 | 2.5 | 2.7 | 2.8 |
| Phosphate 3 $Ca^{2+}$ | 2.2 | 2.5 | 2.9 | 2.8 |
| Gly-Gly 0 $Ca^{2+}$ | 2.3 | 2.6 | 3.1 | — |
| Gly-Gly 1 $Ca^{2+}$ | 2.1 | 2.5 | 2.9 | 3.0 |
| Gly-Gly 2 $Ca^{2+}$ | 2.3 | 2.5 | 2.5 | 2.8 |

TABLE 9-continued

Formation of RP-impurities at 25° C.

| | Storage time (weeks) | | | |
|---|---|---|---|---|
| Test system | 0 (% impurities) | 4 (% impurities) | 6 (% impurities) | 8 (% impurities) |
| Gly-Gly 3 $Ca^{2+}$ | 2.0 | 2.4 | 2.6 | 2.5 |

TABLE 10

Formation of RP-impurities at 37° C.

| | Storage time (weeks) | | | |
|---|---|---|---|---|
| Test system | 0 (% impurities) | 4 (% impurities) | 6 (% impurities) | 8 (% impurities) |
| Phosphate 0 $Ca^{2+}$ | 2.4 | 3.0 | 2.9 | 3.7 |
| Phosphate 1 $Ca^{2+}$ | 2.3 | 3.1 | 3.2 | 3.4 |
| Phosphate 2 $Ca^{2+}$ | 2.4 | 3.0 | 3.2 | 3.6 |
| Phosphate 3 $Ca^{2+}$ | 2.2 | 3.1 | 3.4 | 3.6 |
| Gly-Gly 0 $Ca^{2+}$ | 2.3 | 3.4 | 3.7 | 4.5 |
| Gly-Gly 1 $Ca^{2+}$ | 2.1 | 3.0 | 3.4 | 4.3 |
| Gly-Gly 2 $Ca^{2+}$ | 2.3 | 2.9 | 3.1 | 4.0 |
| Gly-Gly 3 $Ca^{2+}$ | 2.0 | 2.8 | 3.1 | 4.2 | pH

The pH values of the phosphate and Gly—Gly buffers were compared at 25° C. and 37° C., and it was found that the buffer effect of Gly—Gly was comparable to that of the phosphate buffer.

Conclusion

The effect of $Ca^{2+}$ on the dimer formation has been shown to be most pronounced for the Gly—Gly system at 4° C., compared to a phosphate buffer system. This is an important finding in light of the fact that insulin is typically stored at low temperatures of approximately 4–5° C. The addition of 2–3 $Ca^{2+}$ per $(NN304)_6(Zn^{2+})_2$ resulted in an approximately threefold decrease of the dimer formation for the Gly—Gly system, but only about a 20% decrease for the phosphate system at 4° C. The rate of dimer formation is approximately identical for the two buffer systems without $Ca^{2+}$ at 4° C.

The polymer formation was negligible at 4 and 25° C. for the observation periods used. Polymer formation after 6 weeks at 37° C. was decreased by about 30% by addition of 2–3 $Ca^{2+}$ per $(NN304)_6(Zn^{2+})_2$ for both the Gly—Gly and the phosphate system.

$Ca^{2+}$ has no or perhaps only a small effect on the formation of RP-impurities.

Based on the results presented above and the fact that formation of dimers and polymers constitutes a major chemical degradation pathway for insulin, it can be concluded that a combination of metal ions such as $Ca^{2+}$ and a buffer such as Gly—Gly is advantageous as a stabilizer for aqueous insulin compositions.

EXAMPLE 2

Tests were carried out in a similar manner as described above using "NN304" insulin (although a different batch than in Example 1), using either TRIS (7 mM) or Gly—Gly (7 mm) as the buffer and with the addition of either $Mg^{2+}$ or $Ca^{2+}$ as the metal ions. The test systems were prepared as described above and stored for a total of 48 weeks at a temperature of 5° C. The amount of dimer formation was determined after 0, 8, 16, 24, 32 and 48 weeks, and a k-value (% dimer/week) was determined using a linear regression. The systems tested and the results are shown in Table 11 below.

TABLE 11

Dimer formation in different systems at 5° C.

| | Storage time (weeks) | | | | | | |
|---|---|---|---|---|---|---|---|
| Test system | 0 % dimer | 8 % dimer | 16 % dimer | 24 % dimer | 32 % dimer | 48 % dimer | k % dimer/week |
| Gly—Gly no metal ion | 0.05 | 0.10 | 0.17 | 0.16 | 0.23 | 0.20 | 0.0033 |
| TRIS no metal ion | 0.05 | 0.09 | 0.10 | 0.14 | 0.17 | 0.16 | 0.0025 |
| Gly—Gly 1 $Mg^{2+}$/hexamer | 0.05 | 0.08 | 0.09 | 0.10 | 0.14 | 0.12 | 0.0016 |
| Gly—Gly 2 $Mg^{2+}$/hexamer | 0.04 | 0.06 | 0.09 | 0.08 | 0.11 | 0.10 | 0.0013 |
| Gly—Gly 3 $Mg^{2+}$/hexamer | 0.04 | 0.06 | 0.09 | 0.10 | 0.13 | 0.10 | 0.0015 |
| TRIS 2 $Ca^{2+}$/hexamer | 0.05 | 0.07 | 0.09 | 0.11 | 0.13 | 0.13 | 0.0018 |
| TRIS 2 $Mg^{2+}$/hexamer | 0.05 | 0.08 | 0.08 | 0.10 | 0.13 | 0.12 | 0.0015 |

The results above show that the addition of $Mg^{2+}$ to a Gly—Gly system results in a significant reduction of the rate of dimer formation. A reduction in the dimer formation is also seen by addition of $Ca^{2+}$ or $Mg^{2+}$ to the TRIS system, although the relative reduction in the TRIS system is smaller than for the Gly—Gly system. This example thus supports the conclusion above in Example 1, and further illustrates the advantageous effect of using calcium or magnesium ions together with a buffer such as Gly—Gly for stabilizing aqueous insulin compositions.

What is claimed is:

1. An aqueous insulin composition comprising human insulin or an analogue or derivative thereof, glycylglycine buffer, and metal ions selected from the group consisting of calcium and magnesium ions.

2. The composition of claim 1, comprising 0.1–10 metal ions per hexamer of insulin or insulin analogue or derivative.

3. The composition of claim 2, comprising 0.5–5 metal ions per hexamer of insulin or insulin analogue or derivative.

4. The composition of claim 3, comprising 1–4 metal ions per hexamer of insulin or insulin analogue or derivative.

5. The composition of claim 1, wherein the metal ions are calcium ions.

6. The composition of claim 1, wherein the concentration of glycylglycine is in the range of 1–20 mM.

7. The composition of claim 6, wherein the concentration of glycylglycine is in the range of 3–15 mM.

8. The composition of claim 7, wherein the concentration of glycylglycine is in the range of 4–10 mM.

9. The composition of claim 5, wherein the concentration of glycylglycine is in the range of 4–10 mM.

10. The composition of claim 1, comprising a derivative of human insulin or an analogue thereof having at least one lipophilic substituent.

11. The composition of claim 10, comprising an acylated insulin derivative.

12. The composition of claim 11, comprising an insulin derivative wherein the $\epsilon$-amino group of $Lys^{B29}$ contains an acyl substituent comprising at least 6 carbon atoms.

13. The composition of claim 11, wherein the insulin derivative is selected from the group consisting of $N^{\epsilon B29}$-myristoyl-des(B30) human insulin, $N^{\epsilon B29}$-palmitoyl-des(B30) human insulin, $N^{\epsilon B29}$-myristoyl human insulin, $N^{\epsilon B29}$-palmitoyl human insulin, $N^{\epsilon B28}$-myristoyl $Lys^{B28}$ $Pro^{B29}$ human insulin, $N^{\epsilon B28}$-palmitoyl $Lys^{B28}$ $Pro^{B29}$ human insulin, $N^{\epsilon B30}$-myristoyl-$Thr^{B29}Lys^{B30}$ human insulin, $N^{\epsilon B30}$-palmitoyl-$Thr^{B29}Lys^{B30}$ human insulin, $N^{\epsilon B29}$-(N-palmitoyl-$\gamma$-glutamyl)-des(B30) human insulin, $N^{\epsilon B29}$-(N-lithocholyl-$\gamma$-glutamyl)-des(B30) human insulin, $N^{\epsilon B29}$-($\omega$-carboxyheptadecanoyl)-des(B30) human insulin, and $N^{\epsilon B29}$-($\omega$-carboxyheptadecanoyl) human insulin.

14. The composition of claim 13, wherein the insulin derivative is $N^{\epsilon B29}$-myristoyl-des(B30) human insulin.

15. The composition of claim 9, wherein the insulin derivative is selected from the group consisting of $N^{\epsilon B29}$-myristoyl-des(B30) human insulin, $N^{\epsilon B29}$-palmitoyl-des(B30) human insulin, $N^{\epsilon B29}$-myristoyl human insulin, $N^{\epsilon B29}$-palmitoyl human insulin, $N^{\epsilon B28}$-myristoyl $Lys^{B28}$ $Pro^{B29}$ human insulin, $N^{\epsilon B28}$-palmitoyl $Lys^{B28}$ $Pro^{B29}$ human insulin, $N^{\epsilon B30}$-myristoyl-$Thr^{B29}Lys^{B30}$ human insulin, $N^{\epsilon B30}$-palmitoyl-$Thr^{B29}Lys^{B30}$ human insulin, $N^{\epsilon B29}$-(N-palmitoyl-$\gamma$-glutamyl)-des(B30) human insulin, $N^{\epsilon B29}$-(N-lithocholyl-$\gamma$-glutamyl)-des(B30) human insulin, $N^{\epsilon B29}$-($\omega$-carboxyheptadecanoyl)-des(B30) human insulin, and $N^{\epsilon B29}$-($\omega$-carboxyheptadecanoyl) human insulin.

16. The composition of claim 10, comprising a derivative of human insulin having Lys at position B28 and wherein the $\epsilon$-amino group of $Lys^{B28}$ contains an acyl substituent comprising at least 6 carbon atoms.

17. The composition of claim 16, wherein the insulin derivative is $N^{\epsilon B28}$-myristoyl $Lys^{B28}$ $Pro^{B29}$ human insulin or $N^{\epsilon B28}$-palmitoyl $Lys^{B28}$ $Pro^{B29}$ human insulin.

18. A parenteral pharmaceutical formulation comprising an insulin composition of claim 1 and a preservative.

19. A method for improving the stability of an insulin composition comprising human insulin or an analogue or a derivative thereof, which method comprises adding to said composition a glycylglycine buffer and metal ions selected from the group consisting of calcium and magnesium ions.

* * * * *